United States Patent [19]
Heacock

[11] Patent Number: 5,861,939
[45] Date of Patent: Jan. 19, 1999

[54] PORTABLE FUNDUS VIEWING SYSTEM FOR AN UNDILATED EYE

[75] Inventor: Gregory Lee Heacock, New York, N.Y.

[73] Assignee: Odyssey Optical Systems, LLC, Boston, Mass.

[21] Appl. No.: 951,535

[22] Filed: Oct. 16, 1997

[51] Int. Cl.[6] .................................................. A61B 3/10
[52] U.S. Cl. ........................ 351/218; 351/215; 351/221
[58] Field of Search .................................. 351/218, 215, 351/221, 205, 246, 206, 211; 354/62

[56] References Cited

U.S. PATENT DOCUMENTS

| | | |
|---|---|---|
| 4,768,874 | 9/1988 | Webb et al. . |
| 4,877,322 | 10/1989 | Hill .......................................... 351/221 |
| 5,576,780 | 11/1996 | Yancey ..................................... 351/211 |

*Primary Examiner*—Hung Xuan Dang
*Attorney, Agent, or Firm*—McAndrews, Held & Malloy, Ltd.

[57] ABSTRACT

The system of the present invention allows the fundus of an undilated eye to be viewed extremely easily and without the need for the viewer to align a hand held unit with a head mounted unit. The system for viewing the fundus of an undilated eye in accordance with the present invention includes a number of point sources of light that are individually actuable and arranged in a linear array. A lens converts each point of light to a line of light. The point sources of light are sequentially actuated, i.e. turned on and off in sequence, so as to scan the fundus of the undilated eye with lines of light that are directed from the lens to the eye by an optical system. The optical system directs light reflected from the fundus to an image generating apparatus that is responsive to the reflected light to provide an image of the fundus that can be viewed.

43 Claims, 4 Drawing Sheets

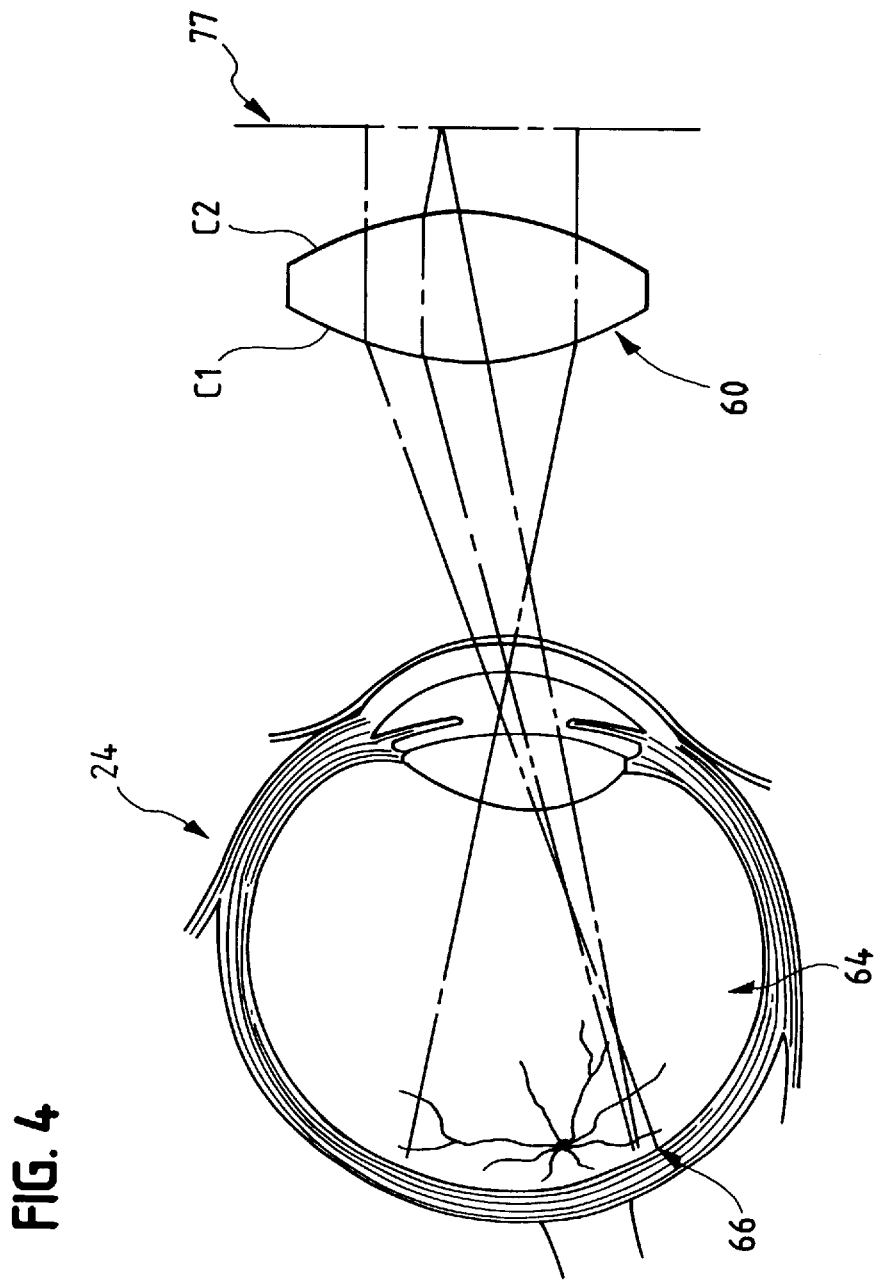

PORTABLE FUNDUS VIEWING SYSTEM FOR AN UNDILATED EYE

TECHNICAL FIELD

The present invention is directed to a fundus viewing system and more particularly to such a system for easily viewing the fundus of an undilated eye.

CROSS-REFERENCE TO RELATED APPLICATIONS

This application is related to U.S. patent application Ser. No. 08/631,969 filed Apr. 15, 1996 and issued Sep. 30, 1997 as U.S. Pat. No. 5,673,097.

STATEMENT REGARDING FEDERALLY SPONSORED RESEARCH OR DEVELOPMENT

N/A.

BACKGROUND OF THE INVENTION

Binocular indirect microscopes (BIOM) are known that allow a doctor to observe the interior of the patient's eye and in particular the fundus of the patient's eye. A BIOM typically includes a binocular prism set with an integral illumination system forming a unit that is worn on the doctor's head, the illumination system including a light bulb and a mirror to direct the light. The BIOM also includes a hand held condensing lens or indirect lens of the type manufactured by Volk, Inc. In use, the doctor positions the binocular prism/illumination system on his head so that he can look through the prisms. The doctor holds the condensing lens in close proximity to the patient's eye to be examined. The doctor then adjusts both the position of the condensing lens and his position so that he can look into the patient's eye through the hand held lens and through the head mounted binocular prisms with the interior of the eye being illuminated by the head mounted illumination system. The BIOM generates a real image of the patient's fundus that is observed by the doctor via the prisms and condensing lens.

Although the BIOM was invented in 1911 by Gullstrand, it is still used today with little change, the improvements over the earlier systems resulting from better optical manufacturing techniques and the use of anti-reflection coatings. Both the early and modern BIOMs share the same problems. In particular, for a BIOM examination, the patient's pupil must be dilated with mydriatic drugs in order for the doctor to view the patient's fundus. As a result, the patient's pupils are unable to respond to varying light levels for several hours; the patient is dazzled by bright lights; under dark conditions the patient has difficulty seeing; and the patient's ability to read is dramatically hampered. BIOMs are also difficult to use because the image produced by the condensing lens is indirect and therefore upside down with left and right reversed. Further, there is an increased possibility of misdiagnosis with a BIOM since the clinician must interpret the upside down/left-right reversed image relative to the patient's real orientation. Also, since the patient's eye, hand held condensing lens, head mounted prisms and the doctors eyes must be aligned coaxially to perform an examination, the physician must typically undergo various positioning maneuvers before the necessary alignment is obtained to conduct the examination.

BRIEF SUMMARY OF THE INVENTION

In accordance with the present invention the disadvantages of prior systems for observing the fundus of an eye have been overcome. The system of the present invention allows the fundus of an undilated eye to be viewed extremely easily and without the need for the viewer to align a hand held unit with a head mounted unit.

More particularly, the system for viewing the fundus of an undilated eye in accordance with the present invention includes a number of point sources of light that are individually actuable and arranged in a linear array. A lens converts each point of light to a line of light. The point sources of light are sequentially actuated, i.e. turned on and off in sequence, so as to scan the fundus of the undilated eye with lines of light that are directed from the lens to the eye by an optical system. The optical system directs light reflected from the fundus to an image generating apparatus that is responsive to the reflected light to provide an image of the fundus that can be viewed.

The system of the present invention is extremely small and can be held in the viewer's hand. The hand held unit may include an eyepiece lens through which the doctor looks to view the interior of the eye directly. Alternatively, the image generating apparatus may include a display that is separate from the hand held unit and that forms a part of a head mounted display unit worn by the viewer. In this embodiment, the doctor can view an enlarged image of the fundus while seeing the patient but without requiring the doctor to align his eyes with the eyes of the patient or the hand held unit. The image generating apparatus may also include a printer to print an image of the fundus so that a permanent record of the fundus image is obtained.

These and other advantages and novel features of the present invention, as well as details of an illustrated embodiment thereof, will be more fully understood from the following description and drawings.

BRIEF DESCRIPTION OF THE SEVERAL VIEWS OF THE DRAWING

FIG. 4 is a raytrace diagram of the objective lens used in the hand held unit of the present invention to form a real image of the patient's fundus.

DETAILED DESCRIPTION OF THE INVENTION

Figure 1:
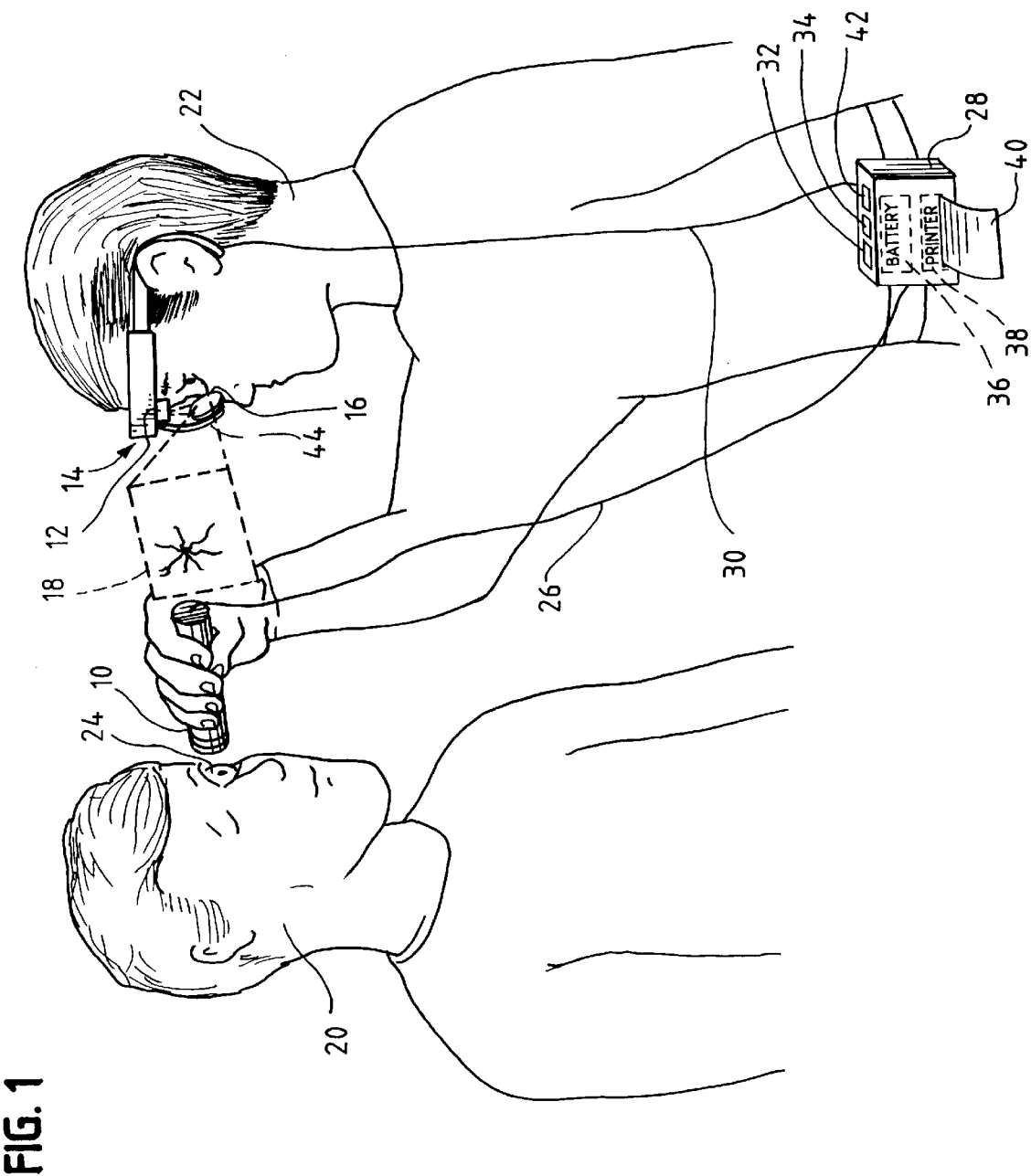
FIG. 1 is a perspective view illustrating one embodiment of the present invention including a hand held unit for scanning an undilated eye with light and for generating an image of the fundus from the light reflected thereto, the hand held unit being coupled to a head mounted display for receiving signals representing the fundus image and for displaying the image.

The system of the present invention as depicted in FIG. 1 includes a hand held unit 10 for providing scanned light to illuminate the interior of an undilated eye and for generating an image of the fundus from the light reflected from the eye as detected in the unit 10. Signals representing the fundus image are coupled from the hand held unit 10 to a display 12 of a head mounted display system 14. The head mounted display system 14 includes an optical system 16 to project an enlarged image 18 of the fundus at a distance from the clinician 22 but between the clinician and the patient 20. In order to use the system of the present invention, the hand held unit 10 is positioned near the cornea of the eye 24 so that the scanned light passes through the pupil of the eye 24 to illuminate the interior of the eye. With the scanning and optical system of the hand held unit 10 as described in detail below, an image of the fundus of the eye 24 is obtained without dilating the eye. Further, only the hand held unit 10 needs to be moved into position with respect to the patient's eye 24. The doctor with the head mounted display system 14 is able to view the image of the fundus at any position.

The hand held unit 10 generates signals representing the detected image of the fundus. These signals can be coupled directly to the display 12 or they can be coupled via a cable 26 to a portable interface unit 28 and from the unit 28, the signals can be coupled to the display 12 via a cable 30. The interface unit 28 is preferably portable and such that it can be body worn such as by mounting the unit on a user's belt. The interface unit 28 includes an on/off switch 32 for the hand held unit 10 and the display 12 as well as a brightness control knob 34 for the display 12. In order to reduce the weight of the hand held unit 10 and the weight of the head mounted unit 14, the interface unit 28 also contains one or more batteries 36 for providing power to the head mounted display 12 via the cable 30 and for providing power to the hand held unit 10 via the cable 26. In one embodiment of the present invention, the interface unit 28 also includes a printer 38, such as a video printer from NEC Inc., that is responsive to the video signals generated by the hand held unit 10 to print an image of the fundus on paper 40 in response to the actuation of a switch 42.

Many variations of the system of the present invention may be made without departing from the scope thereof. For example, the battery powering both the unit 10 and the head mounted display system 14 may be contained in the housing of the hand held unit 10 with the video signals representing the image of the fundus being coupled directly to the display 12 so as to eliminate the need for the interface unit 28. Further, the printer 38 need not be contained in the portable interface unit 28 but may be a desktop unit or the like that communicates with the hand held unit 10 and/or interface unit 28 via a wired connection or via wireless communications using for example radio frequency transmitters and receivers or transceivers. It is noted that wireless communications may also be used to eliminate one or more of the cables depicted in FIG. 1 between the hand held unit 10 and the display 12.

Any known head mounted display system may be used for the unit 14 including a binocular head mounted display system as well as monocular head mounted display system. However, a preferred system is shown in U.S. Pat. No. 5,539,422 wherein the optical element 16 should be moved into the central field of view of one eye of the user. In the preferred embodiment, the optical element 16 is not a see-through element but has a fully reflective mirror surface 44 so as to reflect the image presented on the surface of the display 12 to the viewers eye. The optical element 16 is shaped so as to project an enlarged virtual image of the image depicted on the display 12 so that the virtual image appears at a distance from the clinician 22 but so that it is between the patient 20 and the clinician. The optical element 16 is a monocular optic in that the image depicted on the display 12 is viewed by only one eye of the clinician 22. Further, the optical element 16 is preferably such that it does not take up the entire field of view of the clinician's virtual image viewing eye. The peripheral vision of the image viewing eye is preferably free from obstruction by the optical element 16 so that the virtual image appears to the clinician fused with the real world. The head mounted display system thus allows the clinician to see the patient 20 as well as the hand held unit 10 while viewing the virtual image 18 of the fundus which appears to float between the patient 20 and the clinician 22.

Figure 2:
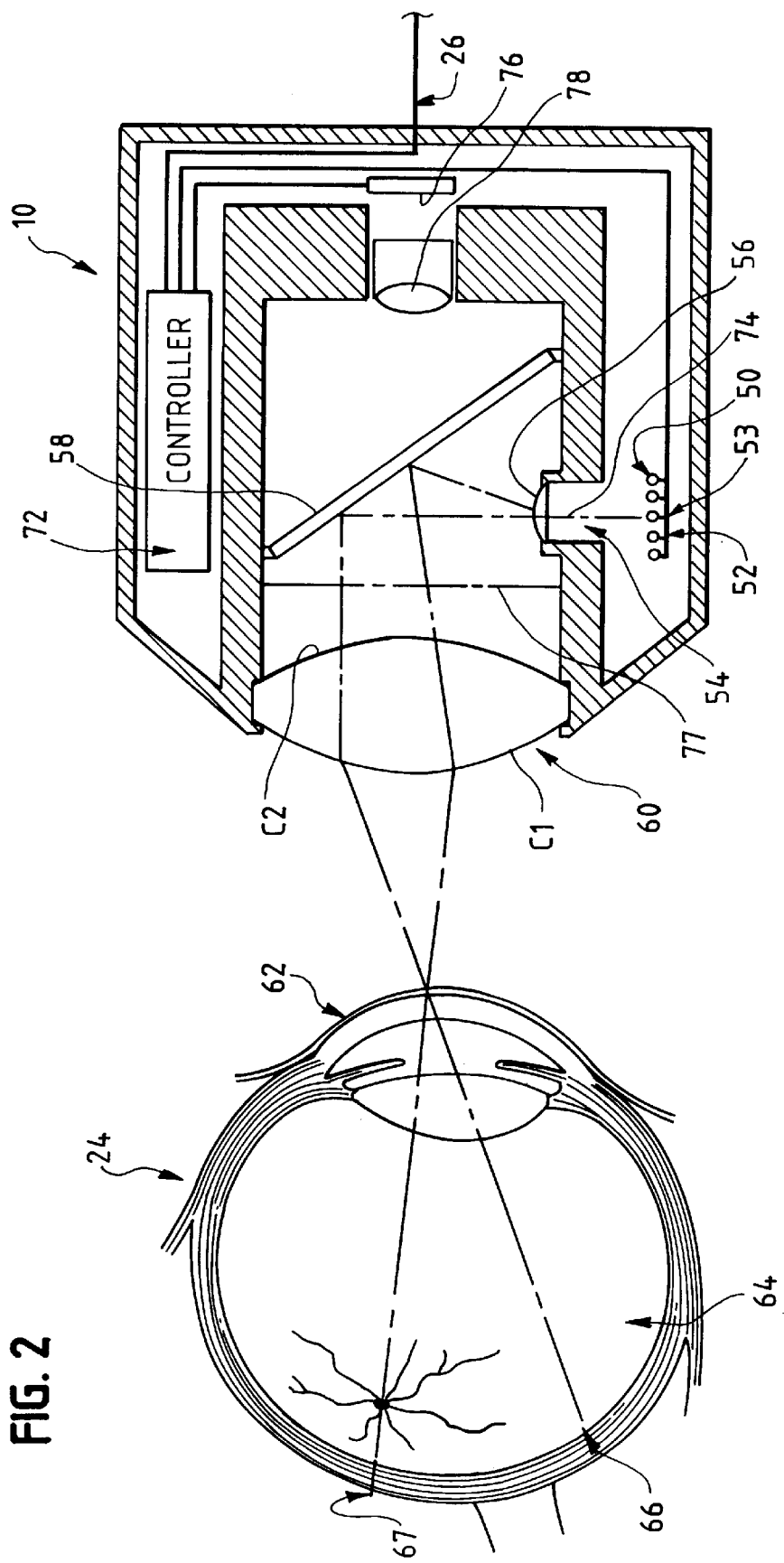
FIG. 2 is a top cross-sectional view of the hand held unit of FIG. 1 illustrating the scanning of light to illuminate the interior of an eye.
Figure 3:
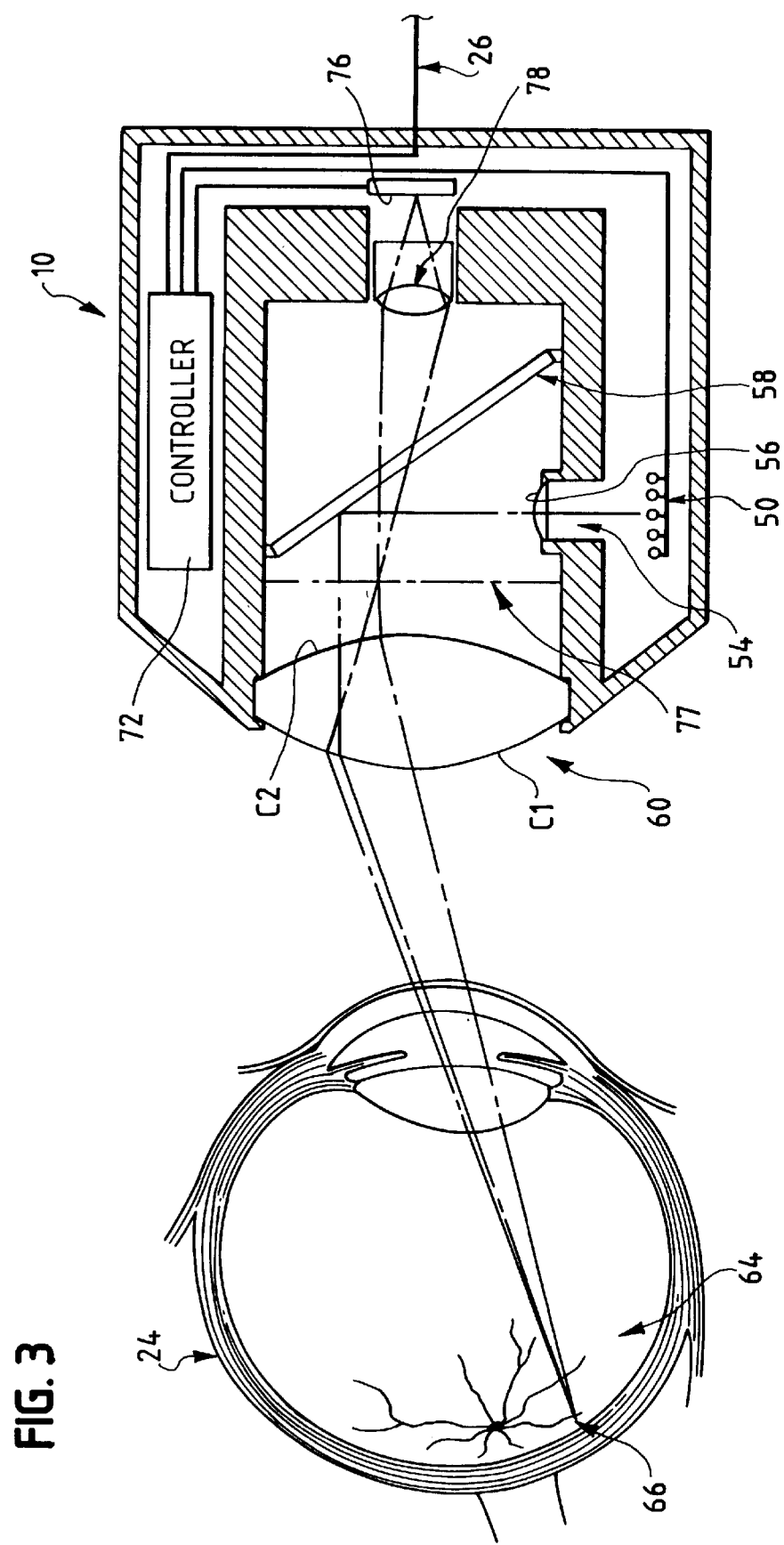
FIG. 3 is a top cross-sectional view of the hand held unit of FIG. 1 illustrating the generation of an image of the fundus of an undilated eye on a CCD camera.

The hand held unit 10 for providing scanned light to illuminate the interior of an undilated eye and for generating an image of the fundus of the eye from the light reflected therefrom is shown in detail in FIGS. 2 and 3. A raytrace illustrating the formation of a real image of the fundus is depicted in FIG. 4. The hand held unit 10 includes a linear array of light emitting diodes (LEDs) 50 to provide a line of point sources of light that can be individually actuated in a sequence. Although each point source of light in the array 50 generates non-coherent light, a linear array of coherent light sources such as laser diodes may also be employed. The light from each of the LEDs 50 passes through a slit aperture 54 to a cylindrical lens 56 wherein the width of the slit 54 is parallel to a diameter of the lens 56. The cylindrical lens 56 converts a point of light from one point source in the array 50 to a line of light that is reflected by a partially reflective mirror 58 to an objective lens 60. The line of light is directed by the objective lens 60 so that it passes through the cornea 62 of the eye 24 illuminating the fundus 64 of the eye. The line of light generated by the lens 56 for a single point of light from the array 50 is such that when it is projected onto the mirror 58, the line of light extends in a direction that is perpendicular to the line of light which would be projected on the mirror 58 if the lens 56 were removed and all of the LEDs in the array 50 were turned on simultaneously.

A controller 72 is coupled to the array of LEDs 50 so as to actuate, i.e. turn on and turn off, each LED 52 in the array 50 in sequence so that, for example, the LED 52 is turned on and when the LED 52 is turned off, the adjacent LED 53 is turned on, etc. The sequential actuation of the LEDs in the linear array 50 causes a series of lines to be scanned across the fundus 64 of the eye 24 so that vertical lines of illumination appear to move from the position 67, for example, across the width of the eye to the position 66 on the fundus 64. Any type of controller 72 may be used to sequentially actuate the point sources of light in the array 50. The controller 72 may include a timer coupled to a counter that actuates a switching array coupled to the LEDs 50. Alternatively a more sophisticated controller such as a microprocessor or the like may be used. The rate of the scan of illumination generated by the controller 72, the light array 50 and cylindrical lens 56 with the slit aperture 54 is preferably between 70 hz and 90 hz.

The objective lens 60 not only directs the scanned illumination to the eye 24 but receives the light reflected from the fundus 64 of the eye 24 and focuses the light at a real image plane 77 inside the hand held unit 10. The reflected rays of light from the fundus 64 pass through the partially reflective mirror 58 and are brought to a focus on a detector area of a CCD camera 76 by a focusing lens 78. The CCD camera 76 is responsive to the light impinging on the detector area thereof for generating video signals representing the impinging light which in turn represents an image of the fundus 64 of the undilated eye 24.

It has been found that by orienting the scanning of the lines of light onto the patient's eye in a particular manner with respect to the orientation of the raster lines of the CCD camera 76, beating and blanking problems in the video image depicted on the display 12 are eliminated. More particularly, the raster lines of the CCD camera 76 extend in one direction, across the CCD camera. A single line of light from the lens 56, when reflected by mirror 58 onto the eye 24, extends in a second direction, generally perpendicular to the direction of the raster lines of the CCD camera 76, but is scanned by the sequential actuation of the LED's in the array 50 in a direction perpendicular to this second direction, i.e. in a direction parallel to the raster lines of the CCD camera 76. Because the line of light scanned onto the patient's eye 24 extends perpendicular to the direction of the raster line of the CCD camera 76, beating and blanking problems in the displayed video image are eliminated. The video signals from the CCD camera 20 are coupled via cable 26 to the display 12 so as to generate an image of the fundus on the display which can then be viewed via the optic 16 of the head mounted unit 14 by the clinician 22. The video signals representing the image of the fundus generated by the CCD scanner are also coupled via cable 26 to the printer 38 so that a hard copy image of the fundus is provided. It is noted that the hand held unit 10 can be converted into a direct viewing system by replacing the CCD camera 76 with an eyepiece lens through which the clinician looks to view the fundus of the eye 24 directly.

The hand held unit 10 is extremely small. The housing for the unit 10 is cylindrical in shape having a length of approximately 60 mm and a diameter of 28 mm. Although any number of point sources of light may be used in the array 50, a linear array of 8 LEDs had been found sufficient to illuminate substantially all of the fundus 64 of an undilated eye. The slit aperture 54 through which the light passes to the cylindrical lens 56 so as to generate a line of light from a noncoherent point source may be 0.5 mm to 2 mm wide, with the preferred width being approximately 1 mm. The cylindrical lens 56 is positioned in the unit 10 so that the center 74 of the back surface of the lens 56 is one focal length from the real image plane 77 as measured from the lens 56 to the partially reflective mirror 58 and from the mirror 58 to the real image planes 77. The objective lens 60 has a diameter of approximately 28 mm. The surfaces $C_1$ and $C_2$ are both defined by the following equation:

$$f(C,cc,z) = Cz^2/(\sqrt{1 - C^2ccz^2}\ )$$

where $C=C_1=0.067$ and $cc=-0.113$; and $C=C_2=-0.04$ and $cc=0.435$ with a magnification factor of 1.0× and a diameter to focal length ratio, f>0.6.

Many modifications and variations of the present invention are possible in light of the above teachings. For example, as noted above, each point source of light need not be of noncoherent light but may be a source of coherent light such as a laser diode. In the event that coherent light is used, the slit aperture 54 can be eliminated. Further, although a cylindrical lens 56 is depicted for converting a point of light to a line of light, other lens may be used to generate a line of light from the point source of light. Non-passive scanners may also be used in place of the passive scanner in the form of lens 56. For example, an acousto optical scanner or a scanner with a moving mirror may be employed. Further, the positions of the image generating system (including CCD camera 76) and the illumination system (including array 50 and lens 56) may be interchanged. Thus, it is to be understood, within the scope of the appended claims, the invention may be practiced otherwise than as described hereinabove.

What is claimed and desired to be secured by Letters Patent is:

1. A portable system for viewing the fundus of an undilated eye comprising:

a plurality of point sources of noncoherent light individually actuable and arranged in a line;

a scanner for converting a point of light from said sources to a line of light;

an optical system for directing light from said scanner to an undilated eye;

a controller for sequentially actuating said point sources of light to scan the fundus of the eye with lines of light directed to the eye by said optical system;

an image detector for receiving light reflected from the fundus and said detector generating signals representing the image of the fundus; and a display responsive to said signals for displaying an image of the fundus.

2. A portable system for viewing the fundus of an undilated eye as recited in claim 1 wherein said point sources of light include a linear array of light emitting diodes.

3. A portable system for viewing the fundus of an undilated eye as recited in claim 1 wherein said scanner is a passive scanner.

4. A portable system for viewing the fundus of an undilated eye as recited in claim 1 wherein said scanner is a cylindrical lens.

5. A portable system for viewing the fundus of an undilated eye as recited in claim 1 wherein said optical system includes an objective lens and a partially reflective mirror, said mirror being disposed between said sources of light and said image detector so that the central axis of the sources of light is generally perpendicular to the central axis of the image detector.

6. A portable system for viewing the fundus of an undilated eye as recited in claim 5 wherein said objective lens focuses light from the sources of light on an area of the patient's eye and said objective lens intercepts light reflected from the patient's eye and focuses the intercepted light onto an image plane disposed between the objective lens and the image detector.

7. A portable system for viewing the fundus of an undilated eye as recited in claim 1 wherein said image detector is a CCD camera.

8. A portable system for viewing the fundus of an undilated eye as recited in claim 1 wherein said sources of light, scanner, optical system and image detector are contained in a housing forming a unit that is hand held in use and said display forms a portion of a head mounted display system that is in communication with said hand held unit.

9. A portable system for viewing the fundus of an undilated eye comprising:

a plurality of point sources of light individually actuable and arranged in a line;

a lens for converting a point of light from said sources to a line of light;

an optical system for directing light from said lens to an undilated eye;

a controller for sequentially actuating said point sources of light to scan the fundus of the eye with lines of light directed to the eye by said optical system;

an image detector for receiving light reflected from the fundus and directed to the detector by said optical system, said detector generating signals representing the image of the fundus; and a display responsive to said signals for displaying an image of the fundus.

10. A portable system for viewing the fundus of an undilated eye as recited in claim 9 wherein said sources of light generate noncoherent light and said system further includes a slit aperture through which said light passes to said lens.

11. A portable system for viewing the fundus of an undilated eye as recited in claim 9 wherein said lens is a cylindrical lens.

12. A portable system for viewing the fundus of an undilated eye as recited in claim 9 wherein said optical system includes an objective lens and a partially reflective mirror, said mirror being disposed between said sources of light and said image detector so that the central axis of the sources of light is generally perpendicular to the central axis of the image detector.

13. A portable system for viewing the fundus of an undilated eye as recited in claim 9 wherein said sources of light, lens, optical system and image detector are contained in a housing forming a unit that is hand held in use and said display forms a portion of a head mounted display system that is in communication with said hand held unit.

14. A system for viewing the fundus of an undilated eye comprising:
- a linear array of a plurality of light emitting diodes;
- a cylindrical lens for receiving light from said array through a slit aperture to generate a line of light;
- an optical system for directing light from said lens to an undilated eye;
- a controller for sequentially actuating said light emitting diodes to scan the fundus of the eye with lines of light directed to the eye by said optical system; and
- image generating apparatus for receiving light reflected from the fundus and directed to the image generating apparatus by said optical system to provide an image of the fundus.

15. A system for viewing the fundus of an undilated eye as recited in claim 14 wherein said image generating apparatus includes an image detector for receiving light reflected from the fundus to generate signals representing the image of the fundus and a display responsive to said signals for displaying an image of the fundus.

16. A system for viewing the fundus of an undilated eye as recited in claim 14 wherein said image generating apparatus includes an image detector for receiving light reflected from the fundus to generate signals representing the image of the fundus and a printer responsive to said signals for printing an image of the fundus.

17. A system for viewing the fundus of an undilated eye as recited in claim 14 wherein said image generating apparatus includes an eyepiece lens through which one person looks to view the fundus of another person.

18. A system for viewing the fundus of an undilated eye as recited in claim 14 wherein said system is portable.

19. A system for viewing the fundus of an undilated eye as recited in claim 18 wherein said linear array of light emitting diodes, cylindrical lens, optical system and at least a portion of said image generating apparatus are housed in a hand held unit.

20. A system for viewing the fundus of an undilated eye comprising:
- a plurality of point sources of light arranged in a linear array and sequentially actuated;
- a lens for converting a point of light from said sources to a line of light;
- an optical system for directing light from said lens to an undilated eye; and
- an image generating apparatus for receiving light reflected from the fundus and directed to the image generating apparatus by said optical system to provide an image of the fundus.

21. A system for viewing the fundus of an undilated eye as recited in claim 20 wherein said system is portable.

22. A system for viewing the fundus of an undilated eye as recited in claim 20 wherein said image generating apparatus includes an image detector for receiving light reflected from the fundus to generate signals representing the image of the fundus and a display responsive to said signals for displaying an image of the fundus.

23. A system for viewing the fundus of an undilated eye as recited in claim 22 wherein said display is a head mounted display.

24. A system for viewing the fundus of an undilated eye as recited in claim 20 wherein said image generating apparatus includes an image detector for receiving light reflected from the fundus to generate signals representing the image of the fundus and a printer responsive to said signals for printing an image of the fundus.

25. A system for viewing the fundus of an undilated eye as recited in claim 20 wherein said image generating apparatus includes an eyepiece lens through which one person looks to view the fundus of another person.

26. A system for viewing the fundus of an undilated eye as recited in claim 20 wherein said sources of light include an array of light emitting diodes.

27. A system for viewing the fundus of an undilated eye as recited in claim 20 including a slit aperture through which light from said sources passes to said lens.

28. A system for viewing the fundus of an undilated eye as recited in claim 20 wherein said lens is a cylindrical lens.

29. A system for viewing the fundus of an undilated eye as recited in claim 20 wherein said sources of light emit coherent light.

30. A system for viewing the fundus of an undilated eye as recited in claim 20 wherein said optical system includes an objective lens and a partially reflective mirror, said mirror being disposed between said sources of light and said image generating apparatus so that the central axis of the sources of light is generally perpendicular to the central axis of the image generating apparatus.

31. A system for viewing the fundus of an undilated eye as recited in claim 30 wherein said objective lens focuses light from the sources of light on an area of the patient's eye and said objective lens intercepts light reflected from the patient's eye and focuses the intercepted light onto an image plane disposed between the objective lens and the image generating apparatus.

32. A portable system for viewing the fundus of an undilated eye comprising:
- a hand held unit for scanning light into an undilated eye to illuminate the fundus of the eye and responsive to light reflected from the eye to generate signals representing an image of the fundus; and
- a head mounted display system responsive to said fundus image signals generated by said hand held unit and including at least one display for displaying an image of the fundus and an associated optical system for projecting the displayed fundus image at a distance from the user of the head mounted system.

33. A portable system for viewing the fundus of an undilated eye as recited in claim 32 wherein said hand held unit includes a linear array of light emitting diodes, said diodes being sequentially actuated; a lens for converting light from each light emitting diode to a line of light; and a slit aperture through which light passes form said array to said lens.

34. A portable system for viewing the fundus of an undilated eye as recited in claim 32 wherein said hand held unit includes a linear array of point sources of laser light, said sources of laser light being sequentially actuated and a lens for converting light from each point source to a line of light.

35. A portable system for viewing the fundus of an undilated eye as recited in claim 32 wherein said hand held unit includes a CCD camera responsive to light reflected from the fundus to generate signals representing an image of the fundus.

36. A portable system for viewing the fundus of an undilated eye as recited in claim 32 including a printer responsive to signals representing said fundus image signals generated by said hand held unit for printing an image of the fundus.

37. A portable system for viewing the fundus of an undilated eye as recited in claim 36 wherein said printer is portable.

38. A system for viewing the fundus of an undilated eye comprising:

- a hand held unit for scanning light into an undilated eye to illuminate the fundus of the eye and responsive to light reflected from the eye to generate signals representing an image of the fundus;
- a display responsive to signals representing said fundus image signals generated by said hand held unit for displaying an image of the fundus; and
- a printer responsive to signals representing said fundus image signals generated by said hand held unit for displaying an image of the fundus.

39. A portable system for viewing the fundus of an undilated eye as recited in claim 38 wherein said hand held unit includes a linear array of light emitting diodes, said diodes being sequentially actuated; a lens for converting light from each light emitting diode to a line of light; and a slit aperture through which light passes form said array to said lens.

40. A portable system for viewing the fundus of an undilated eye as recited in claim 38 wherein said hand held unit includes a linear array of point sources of laser light, said sources of laser light being sequentially actuated and a lens for converting light from each point source to a line of light.

41. A portable system for viewing the fundus of an undilated eye as recited in claim 38 wherein said hand held unit includes a CCD camera responsive to light reflected from the fundus to generate signals representing an image of the fundus.

42. A portable system for viewing the fundus of an undilated eye as recited in claim 38 wherein said display is portable.

43. A portable system for viewing the fundus of an undilated eye as recited in claim 38 wherein said printer is portable.

* * * * *